US006043065A

United States Patent [19]
Kao et al.

[11] Patent Number: 6,043,065
[45] Date of Patent: Mar. 28, 2000

[54] PHOTOSENSITIVE ORGANIC COMPOUNDS THAT RELEASE 2,5,-DI(TERT-BUTYL) HYDROQUINONE UPON ILLUMINATION

[75] Inventors: Joseph P. Y. Kao, Silver Spring, Md.; Francis M. Rossi, Mountain View, Calif.; Paul F. Keitz, Baltimore, Md.

[73] Assignee: University of Maryland Biotechnology Institute, Baltimore, Md.

[21] Appl. No.: 08/997,239

[22] Filed: Dec. 23, 1997

[51] Int. Cl.⁷ .......................... C12N 13/00; C07C 69/96; C07C 41/00
[52] U.S. Cl. ...................... 435/173.1; 558/272; 568/579
[58] Field of Search .......................... 435/173.1; 558/20, 558/44, 70, 260, 270, 272, 275; 560/1, 8, 129, 130; 568/579, 716

[56] References Cited

U.S. PATENT DOCUMENTS 5,430,175  7/1995  Hess et al. .............................. 560/130

OTHER PUBLICATIONS

Rossi et al, *Journal of Biological Chemistry*, 272(6):3266–3271 (1997).
Rossi et al, American Chemical Society, Division of Organic Chemistry, Abstract No. 192, 211th ACS National Meeting, New Orleans, LA (Mar. 24–28, 1996).
Rossi et al, The American Society for Cell Biology, Abstract No. 2038 and Poster, Thirty–fifth Annual Meeting (Dec. 9–13, 1995).
Bervan et al. "A role for a pertussis toxin–sensitive trimeric G–protin in store–operated Ca2+ inflow in hepatocytes," FEBS Lett. 91994) 346: 235–240, 1994.

Kao et al. "'Caged' carbon monoxide: Photolabile molecules that release free carbon monoxide upon illumination," FASEB J. (1995) 9(3): A392.

Kao et al. "Practical aspects of measuring [Ca2+] with fluoroscent indicators," Meth. Cell Biol. (1994) 40: 155–181.

Rossi et al. "N–moc–L–glutamate, a new caged glutamate with high chemical stability and low pre–photolysis activity," J. Biol. Chem. (Dec. 1997) 272(52): 32922–9.

Kao et al. "Photochemically generated cytosolic calcium pulses and their detection by Fluo–3*," J. Biol. Chem. (May 1989) 264(14): 8179–84.

Haugland "Hnadbook of Fluorescent probes and Research Chemicals," (Nov. 16, 1996) 6th edition. (Molecular Probes, Inc.: Eugene OR) p. 447–455.

Muralidharan et al. "Photolabile 'caged' adrenergic receptor agonists and related model compounds," J. Photochem. Photobiol. (1995) 27: 123–137.

*Primary Examiner*—Jon P. Weber
*Assistant Examiner*—Susan Hanley
*Attorney, Agent, or Firm*—Sughrue, Mion, Zinn, Macpeak & Seas, PLLC

[57] ABSTRACT

Derivatives of o-nitromandelyoxycarbonyl (Nmoc) which are capable of releasing 2,5,-di(tert-butyl)hydroquinone (DBHQ) upon irradiation with ultraviolet (UV) light, are disclosed, as well as, a method for producing DBHQ employing the same so as to allow rapid, reversible transient inhibition of sarcoplasmic/endoplasmic reticulum $Ca^{2+}$ ATPases.

14 Claims, 10 Drawing Sheets

PHOTOSENSITIVE ORGANIC COMPOUNDS THAT RELEASE 2,5,-DI(TERT-BUTYL) HYDROQUINONE UPON ILLUMINATION

FIELD OF THE INVENTION

The present invention relates to derivatives of o-nitromandelyoxycarbonyl (Nmoc) which are capable of releasing 2,5,-di(tert-butyl)hydroquinone (DBHQ) upon irradiation with ultraviolet (UV) light, and a method for producing DBHQ employing the same so as to allow rapid, reversible transient inhibition of sarcoplasmic/endoplasmic reticulum $Ca^{2+}$ ATPases.

BACKGROUND OF THE INVENTION

Intracellular concentration and distribution of the ubiquitous second messenger $Ca^{2+}$ is tightly controlled by a number of pathways (Tsien et al, *Ann. Rev. Cell Biol.,* 6:715–760 (1990)). The interaction of the pathways that mobilize and regulate free $Ca^{2+}$ levels can result in highly complex and dynamic signaling patterns, such as $Ca^{2+}$ oscillations and waves (Tsien et al, supra; Berridge et al, *Curr. Opinion Cell Biol.,* 6:267–274 (1994); and Meyer et al, *Ann. Rev. Biophys. Biophys. Chem.,* 20:153–174 (1991)). Pulsed perturbation of the concentrations of various second messengers, achieved by flash photolysis of caged inositol-1,4,5-trisphosphate, diacylglycerol, and $Ca^{2+}$ (Walker et al, *Nature(London),* 327:249–252 (1987); Harootunian et al, *Cell Calcium.,* 12:153–164 (1991a); Adams et al, *J. Am. Chem. Soc.,* 110:3212–3220 (1988); Ellis-Davies et al, *J. Org. Chem.,* 53:1966–1969 (1988); and Ellis-Davies et al, *Proc. Natl. Acad. Sci., USA,* 91:187–191 (1994)), has yielded highly specific mechanistic information about these dynamic phenomena (Harootunian et al, supra; and Harootunian et al, *Science,* 251:75–78 (1991b)). Although the role of second messengers themselves in dynamic signaling phenomena has been studied by photorelease techniques, the contribution of pathways that regulate second messenger levels remains unexplored.

The family of sarcoplasmic/endoplasmic reticulum $Ca^{2+}$ ATPases (hereinafter "SERCA") that sequester $Ca^{2+}$ into the sarcoplasmic reticulum (hereinafter "SR"), and endoplasmic reticulum (hereinafter "ER") are important regulators of cytosolic free $Ca^{2+}$ levels (Lytton et al, *J. Biol. Chem.,* 267:14483–14489 (1992)). It was postulated in the present invention that the effect of these pumps on $Ca^{2+}$ oscillations and waves could be elucidated by the development of a method for the pulsed modulation of their activity. This could be accomplished by the preparation of a caged, reversible SERCA inhibitor.

SERCA inhibitors have been described by Thomas et al, In: *A Practical Guide to the Study of Calcium in Living Cells* (*Meth. Cell Biol.,* 40), Academic Press, San Diego, pp 65–89 (1994). The three most commonly used SERCA inhibitors are thapsigargin (Thastrup et al, *Proc. Natl. Acad. Sci., USA,* 87:2466–2470 (1990); and Lytton et al, *J. Biol. Chem.,* 266:17067–17071 (1991)), cyclopiazonic acid (Goeger et al, *Biochem. Pharmacol.,* 38:3995–4003 (1989)) and DBHQ (Moore et al, *FEBS Lett.,* 224:331–336 (1987); and Kass et al, *J. Biol. Chem.,* 264:15192–15198 (1989)). Because its inhibitory action is irreversible (Sagara et al, *J. Biol. Chem.,* 267:1286–1292 (1992)), thapsigargin is not a suitable target for a caged reagent to be used for reversible photomodulation of SERCA activity. Cyclopiazonic acid has a relatively complex molecular structure and, being a biosynthetic product of fungal origin, is available only in small quantities at high expense, which makes it an unattractive starting material for organic synthesis. In contrast, DBHQ is structurally simple, incorporating only one type of reactive functional group for caging purposes, and is commercially available in large quantities. These advantages, together with its reversibility, made DBHQ the preferred target for caging in the present invention.

The great majority of photoreleasable compounds have used caging groups structurally based on the 2-nitrobenzyl system (Kao et al, In: *Optical Microscopy, Emerging Methods and Applications,* Herman et al, eds., Academic Press, San Diego, pages 27–85 (1993)). Although the simple parent 2-nitrobenzyl moiety is a common caging group, it was not appropriate for caging DBHQ: preliminary experiments indicated that UV irradiation of cells bathed in medium containing 2-nitrobenzyl alcohol resulted in irreversible inhibition of the SERCA pump. Because photolysis of any 2-nitrobenzyl-caged compound is expected to generate the same photochemical byproducts, it was inferred in the present invention that the byproducts of photolyzing a 2-nitrobenzyl-caged DBHQ would not be inert.

It has been shown that the α-carboxy-nitrobenzyl (CNB) group is useful for caging neuroactive amino acids (Milburn et al, *Biochem.,* 28:49–55 (1989); Gee et al, *J. Am. Chem. Soc.,* 116:8366–8367 (1994); Wieboldt et al, *Biochem.,* 33:1526–1533 (1994a); Wieboldt et al, *Proc. Natl. Acad. Sci., USA,* 91:8752–8756 (1994b); and Gee et al, *J. Org. Chem.,* 60:4260–4263 (1995)). Photodeprotection was shown to proceed rapidly and with high quantum yield (Wieboldt et al, (1994b) supra). It was recognized in the present invention that the carboxylate on this caging group would reduce the reactivity of the photochemical byproduct. Furthermore, the presence of the carboxylate offers the added advantages of increasing the water solubility of the caged compound and allowing for the preparation of a caged AM ester, which could be passively loaded into cells.

Caging DBHQ directly with the CNB group requires the formation of a benzyl ether, which model studies indicated was problematic. For example, reaction of DBHQ with 2-nitrobenzyl chloride in the presence of $K_2CO_3$ yielded numerous compounds that were difficult to isolate and characterize. Reasoning that the difficulties encountered in benzyl ether formation were at least partially the result of the sterically congested environment surrounding the phenolic hydroxyl groups of DBHQ, it was postulated in the present invention that an efficacious caging reaction would need to proceed through a different mechanism.

Figure 1:
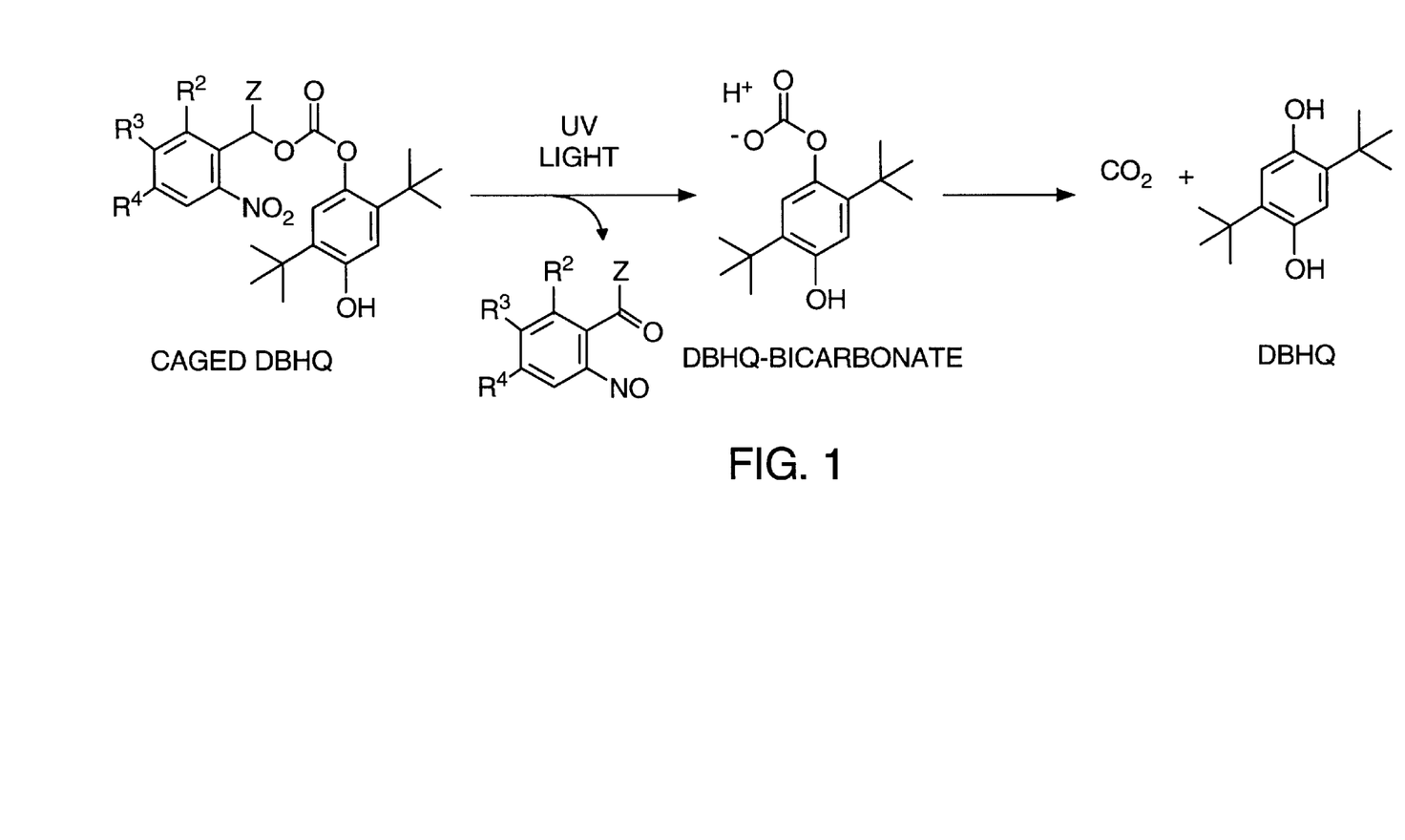
FIG. 1 shows the reaction scheme for the photolysis of the compounds of the present invention.

The o-nitromandelyloxycarbonyl (Nmoc) group was designed in the present invention as a photocleavable caging group that would combine the desirable qualities of the CNB group with a caging reaction that proceeds via carbonyl substitution. As shown in FIG. 1, irradiation of the caged-DBHQ with UV light would result in the formation of DBHQ-bicarbonate, which would rapidly decompose under physiological conditions to DBHQ and carbon dioxide. The photochemical side product, a 2-(2-nitrosophenyl) glyoxylate, is the same as that generated by photolysis of α-CNB-caged molecules (Milburn et al, supra; Gee et al, supra;

Wieboldt et al, (1994a) supra; Wieboldt et al (1994b), supra; and Gee et al, supra), for which no adverse biological effects have ever been reported. Carbon dioxide, liberated by decarboxylation of DBHQ-bicarbonate, is a normal product of metabolism, and would thus also be innocuous.

Thus, the present invention provides caged DBHQ. The compounds of the present invention make it possible to deliver, with temporal precision, controlled doses of DBHQ to spatially restricted sites in living biological samples.

SUMMARY OF THE INVENTION

An object of the present invention is to provide reagents capable of generating DBHQ upon illumination with UV light.

Another object of the present invention is to provide biologically inert compounds which can be taken up by cells, and will remain stable inside of cells until irradiated, at which time DBHQ will be generated inside of the cells.

Still another object of the present invention is to provide a method for rapidly delivering controlled, small doses of DBHQ to spatially restricted sites in living biological samples at physiological temperatures.

These and other objects of the present invention, which will be apparent from the detailed description of the invention provided hereinafter, have been met in one embodiment by a compound represented by Formula (I):

wherein Z is selected from the group consisting of $CO_2R^1$, $SO_3R^1$ and $PO_3R^1{}_2$;

wherein $R^1$ is selected from the group consisting of hydrogen, an alkyl having from 1 to 5 carbon atoms, an alkali metal, preferably Li, Na, K or Cs; $NH_4$, and $CH_2O_2CCH_3$; and wherein $R^2$, $R^3$ and $R^4$, which may be the same or different, are each selected from the group consisting of hydrogen, an alkyl having from 1 to 5 carbon atoms, F, Cl, Br, CN, $NO_2$, $CO_2R^5$, $OR^5$, and $OCH_2CO_2R^5$, wherein $R^5$ is selected from the group consisting of hydrogen, an alkyl having from 1 to 5 carbon atoms, an alkali metal, preferably Li, Na, K or Cs; $NH_4$, and $CH_2O_2CCH_3$; and wherein optionally, $R^3$ and $R^4$ together form a $(O-(CH_2)_n-O)$ linkage, wherein n represents an integer of from 1 to 4, preferably from 1 to 2.

In another embodiment, the above-described objects of the present invention have been met by a method for producing DBHQ comprising the step of UV irradiating a compound represented by Formula (I).

BRIEF DESCRIPTION OF THE DRAWINGS

In FIGS. 5A and 5B, arrow heads and associated numbers indicate, respectively, the times and durations of photolysis light flashes. corresponding dips in the experimental traces are due to temporary interruption of fluorescence data acquisition by an electromechanical shutter to avoid exposure of the fluorescence photomultiplier tube to leakage from the high-intensity photolytic flash. Each plus sign (+) on an experimental trace marks the first intensity datum collected after a photorelease episode. Fluo-3 fluorescence data are presented as the relative intensity, $F(t)/F_0$, where $F(t)$ is the intensity at time t during an experiment, and $F_0$ is the average intensity measured with the cell at rest (prior to photorelease).

In FIGS. 6A and 6B, arrow heads and associated numbers indicate, respectively, the times and durations of photolytic light flashes.

DETAILED DESCRIPTION OF THE INVENTION

As discussed above, in one embodiment, the above-described objects of the present invention have been met by a compound represented by Formula (I).

The compounds of the present invention are biologically inert, can be taken up by cells, and will remain stable until irradiated, at which time DBHQ is released. Thus, a way of instantaneously generating intracellular DBHQ is made available by the compounds of the present invention.

In addition, by using a microscope, light can be narrowly focussed on a sample, even at the single cell level, so that highly localized administration of DBHQ can be achieved. Moreover, because light flashes can be very short and intense, DBHQ can be generated at a precise instant with sub-second time resolution. In addition, varying doses of DBHQ can be delivered by varying the intensity and/or duration of the light flashes, allowing dose-response relationships to be studied. The compounds of the present invention also exhibit little toxicity, and are easily loaded into cells.

In Formula (I), Z is preferably $CO_2R^1$.

$R^1$ is preferably hydrogen, methyl, ethyl, Na, K, Cs or $CH_2O_2CCH_3$.

$R^2$ is preferably hydrogen or $NO_2$.

$R^3$ and $R^4$ are preferably each selected from the group consisting of hydrogen or methoxy, or, when $R^3$ and $R^4$ are combined, methylenedioxy ($-OCH_2-$).

Acetoxymethyl ($CH_2O_2CCH_3$) (AM) esters can be directly loaded into living cells. This is because these esters mask the negative charge on the carboxyl group, and the resulting compounds are neutral and hydrophobic, such that they easily diffuse across biological membranes. Once inside the cells, however, the esters are readily hydrolyzed by non-specific esterases to yield the caged DBHQ molecules, which are negatively charged, and unable to cross biological membranes, and thus become trapped and accumulate inside the cells.

Specific examples of the compounds of the present invention include 1-[2,5-Di(tert-butyl)-4-hydroxyphenyl]-2-[2-[2-nitrophenyl]acetic acid-2-yl] carbonate (Nmoc-DBHQ), 1-[2,5-Di(tert-butyl)-4-hydroxyphenyl]-2-[methyl 2-[2-nitrophenyl]acetate-2-yl] carbonate (Nmoc-DBHQ/Me), 1-[2,5-Di(tert-butyl)-4-hydroxyphenyl]-2-[ethyl 2-[2-nitrophenyl]acetate-2-yl] carbonate (Nmoc-DBHQ/Et), 1-[2,5-Di(tert-butyl)-4-hydroxyphenyl]-2-[sodium 2-[2-nitrophenyl]acetate-2-yl] carbonate (Nmoc-DBHQ/Na), 1-[2,5-Di(tert-butyl)-4-hydroxyphenyl]-2-[potassium 2-[2-nitrophenyl]acetate-2-yl] carbonate (Nmoc-DBHQ/K), 1-[2,5-Di(tert-butyl)-4-hydroxyphenyl]-2-[acetoxymethyl 2-[2-nitrophenyl]acetate-2-yl] carbonate (Nmoc-DBHQ/AM), 1-[2,5-Di(tert-butyl)-4-hydroxyphenyl]-2-[2-[4,5-methylenedioxy-2-nitrophenyl]acetic acid-2-yl] carbonate, 1-[2,5-Di(tert-butyl)-4-hydroxyphenyl]-2-[methyl 2-[4,5-methylenedioxy-2-nitrophenyl]acetate-2-yl] carbonate, 1-[2,5-Di(tert-butyl)-4-hydroxyphenyl]-2-[ethyl 2-[4,5-methylenedioxy-2-nitrophenyl]acetate-2-yl] carbonate, 1-[2,5-Di(tert-butyl)-4-hydroxyphenyl]-2-[sodium 2-[4,5-methylenedioxy-2-nitrophenyl]acetate-2-yl] carbonate, 1-[2,5-Di(tert-butyl)-4-hydroxyphenyl]-2-[potassium 2-[4,5-methylenedioxy-2-nitrophenyl]acetate-2-yl] carbonate, and 1-[2,5-Di(tert-butyl)-4-hydroxyphenyl]-2-[acetoxymethyl 2-[4,5-methylenedioxy-2-nitrophenyl]acetate-2-yl] carbonate.

UV light generally is considered to have a wavelength of 200 to 400 nm. In the present invention, any light within this wavelength range can be employed. However, from the standpoint of biological compatibility, it is preferred that the wavelength employed be in the range of 300 to 400 nm, as UV at wavelengths below 300 nm can damage proteins and nucleic acids in cells.

The temperature at which UV illumination is carried out is not critical to the present invention, and can be any temperature which does not adversely affect living cells. Generally, illumination is carried out at about 10 to 40° C.

The duration of UV illumination is not critical to the present invention, and will depend upon the intensity of the light source. Examples of such light sources include a mercury lamp and a xenon lamp.

The compounds of the present invention can be used in the method of present invention in the form of an aqueous solution. The concentration of the compounds of the present invention in the aqueous solution is not critical to the present invention. Generally, the concentration will be about $10^{-5}$ to $10^{-1}$ M.

The pH of the aqueous solution is not critical to the present invention, and generally is about 6 to 8.

The pH can be maintained using any suitable buffering system, such as a phosphate or N'-2-hydroxyethlypiperazine-N'-2-ethanesulfonate (HEPES) buffer.

The compounds of the present invention can be used in an aqueous bath of culture media so as to perfuse tissues or cultured cells. UV illumination of the culture medium bathing the tissue or cells liberates free DBHQ, which readily crosses biological membranes, and can thus enter the cells.

Alternatively, an aqueous solution of the compounds of the present invention can be introduced into living cells through either microinjection or patch pipets. The caged DBHQ molecules, being negatively charged, are retained in the injected cells. Flashing the cells with UV light will generate DBHQ from within loaded cells.

Alternatively, the compounds of the present invention can be passively loaded into cells through incubation with the corresponding AM ester. Flashing the cells with UV light will generate DBHQ from within the loaded cells.

The compounds of the present invention can be prepared in general by ester formation between a protected and activated caging group (methyl-2-[2-nitrophenyl]acetate-2-oxycarbonylimidazole) with 2,5-di(tert-butyl) hydroquinone. The methyl-protected carboxyl function in the resulting product can be converted to other forms through de-esterification and/or re-esterification.

The compounds of the present invention are useful, inter alia, for probing systems whose rapidly varying $Ca^{2+}$ dynamics make study inaccessible through conventional techniques of reagent delivery.

The following examples are provided for illustrative purposes only and are in no way intended to limit the scope of the present invention.

In the following Synthesis Examples, the reagents and solvents were ACS or HPLC grade and were used as received from Aldrich or Fisher. Dimethylformamide (DMF) and dichloromethane were stored over 3 Å molecular sieves.

All oxygen- and water-sensitive reactions were performed under dry argon atmosphere. For water-sensitive reactions, glassware was dried at 130° C. for at least 3 hr, and cooled under a stream of argon or in a desiccator prior to use.

The products were purified by column chromatography as described by Still et al, *J. Org. Chem.*, 43:2923 (1978), using silica gel 60 (230–400 mesh, E. Merck).

Melting points were recorded on a Melt-temp II (Laboratory Devices) apparatus coupled to an omega (Omega Engineering) HH23 digital thermometer. All of the melting points reported were uncorrected.

The structures of all of the purified products were established by NMR spectral analysis. Spectra were recorded on a General Electric QE-300 (300 MHZ) NMR spectrometer. All of the samples were dissolved in $CDCl_3$ (0.03% (w/v) tetramethylsilane (TMS)) unless otherwise stated, and were referenced to TMS. Samples in solvents other than $CDCl_3$ were referenced to the residual solvent peak. Resonances are reported in the following format: NMR (solvent): chemical shift in ppm downfield from tetramethylsilane, multiplicity (s=singlet, d=doublet, t=triplet, q=quartet, m=multiplet, b=broad), spin-spin coupling constant if appropriate, and integrated number of protons. High resolution mass spectrometric analysis was performed at the University of Maryland, College Park, on a Model VG707E spectrometer (VG Analytical).

SYNTHESIS EXAMPLE 1

Figure 2:
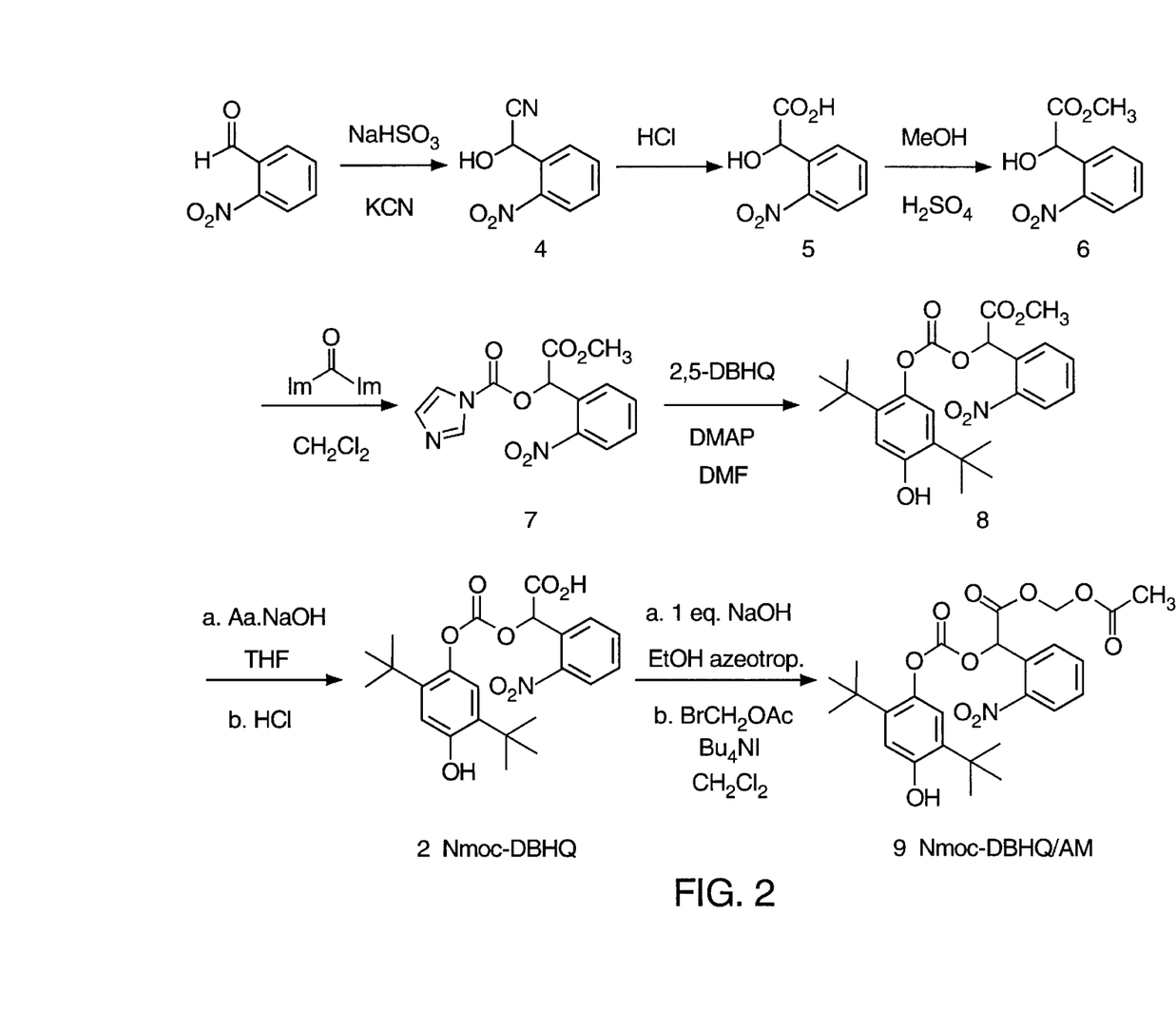
FIG. 2 shows the reaction scheme for the synthesis of Nmoc-DBHQ.

Nmoc-DBHQ was prepared as shown in FIG. 2. In particular, 2-nitrobenzaldehyde was converted to the cyanohydrin (Compound 4), which was hydrolyzed to o-nitromandelic acid (Compound 5) by refluxing in concentrated hydrochloric acid. Methyl o-nitromandelate (Compound 6) was prepared by Fisher esterification of Compound 5. Caging DBHQ necessitated the preparation of an activated o-nitromandelyl-oxycarbonyl group. The oxycarbonyl imidazole derivative (Compound 7) was considered superior to the chloroformate because of its stability and ease of preparation. Treatment of alcohol Compound 6 with carbonyl diimidazole gave Compound 7 in high yield as a stable crystalline solid. The desired carbonate (Compound 8) was formed when a solution of Compound 7 and DBHQ in DMF was heated with a catalytic amount of DMAP. Saponification of the methyl ester (Compound 8)

followed by acidification gave Nmoc-DBHQ (Compound 2). To facilitate loading of the caged reagent into cells, the AM ester of Nmoc-DBHQ (Compound 9) was prepared. Neutralization of Compound 2 with one equivalent of sodium hydroxide, followed by esterification with bromomethyl acetate in the presence of tetrabutylammonium iodide gave Nmoc-DBHQ/AM (Compound 9).

More specifically, 2-hydroxy-2-[2-nitrophenyl] acetonitrile (FIG. 2; Compound 4) was prepared by adding sodium bisulfite (8.26 g, 79 mmol) to a suspension of 2-nitrobenzaldehyde (10 g, 66 mmol) in water (60 ml). After the reaction mixture had stirred for 10 min, it was cooled on ice water. Then, a solution of potassium cyanide (5.16 g, 79 mmol; dissolved in 30 ml of water) was added dropwise. The mixture was stirred for 30 min, warmed to room temperature, and filtered. The solid was washed with water and air dried to give 10 g (85%) of 2-hydroxy-2-[2-nitrophenyl]acetonitrile. The material could be recrystallized from methanol/water. mp. 89–91° C. $^1$H-NMR: 8.21 (d, J=8.06 Hz, 1H), 7.97 (d, J=7.57 Hz, 1H), 7.81 (t, J=7.21 Hz, 1H), 7.66 (t, J=7.82 Hz, 1H), 6.19 (d, J=6.59 Hz, 1H), 3.71 (d, J=6.60 Hz, 1H). HRMS(CI): calculated for $C_8H_7N_2O_3$ [M$^+$+H] m/z=179.0457, observed 179.0453.

2-Hydroxy-2-[2-nitrophenyl]acetic acid (FIG. 2; Compound 5) was prepared by refluxing 2-hydroxy-2-[2-nitrophenyl]acetonitrile (cyanohydrin) (9.5 g, 48 mmol) in concentrated hydrochloric acid (100 ml) for 2.5 hr. The solution was then cooled to room temperature, and extracted with ethyl acetate. The extract was dried over MgSO$_4$, and evaporated, leaving 12.98 g of crude acid, which had acetic acid as an impurity. This was taken on to the methyl ester without further purification.

To prepare pure 2-hydroxy-2-[2-nitrophenyl] acetic acid, cyanohydrin (4.00 g, 22.4 mmol) was refluxed in concentrated hydrochloric acid (40 ml) for 3 hr. The solution was diluted with water (100 ml) and continuously extracted with ether overnight. Evaporation of solvent gave a brown solid, which was digested with isopropyl ether (10 ml), filtered and washed with additional isopropyl ether to give 3.30 g (75%) of 2-hydroxy-2-[2-nitrophenyl]acetic acid as a tan, crystalline solid. mp. 137–139° C. $^1$H-NMR(acetone-d$_6$): 8.06 (d, J=8.02 Hz, 1H), 7.91 (d, J=7.81 Hz, 1H), 7.77 (t, J=7.57 Hz, 1H), 7.61 (t, J=7.82 Hz, 1H), 5.90 (s, 1H). HRMS(CI): calculated for $C_8H_8NO_5$ [M$^+$+H] m/z=198.0403 observed 198.0403.

Methyl 2-hydroxy-2-[2-nitrophenyl]acetate (FIG. 2; Compound 6) was prepared by dissolving crude acid 2-hydroxy-2-[2-nitrophenyl]acetic acid (entire amount) in methanol (100 ml). Sulfuric acid (5 drops) was added, and the mixture was refluxed for 2.5 hr. The solvent was then evaporated. The residue was taken up in ethyl acetate and extracted with saturated sodium bicarbonate, followed by water and brine. After drying over MgSO$_4$, the solvent was evaporated to give 9.13 g (90%) of crude ester which was recrystallized from isopropyl ether to give 7.92 g (78%) of methyl 2-hydroxy-2-[2-nitrophenyl]acetate. mp. 69–71° C. $^1$H-NMR: 8.01 (d, J=8.19 Hz, 1H), 7.70–7.63 (m, 2H), 7.55–7.49 (m, 1H), 5.83 (d, J=4.88 Hz, 1H), 3.76 (s, 3H), 3.66 (d, J=4.89 Hz, 1H). HRMS(CI): calculated for $C_9H_{10}NO_5$ [M$^+$+H] m/z=212.0559, observed 212.0555.

Methyl 2-[2-nitrophenyl]acetate-2-oxycarbonylimidazole (FIG. 2; Compound 7) was prepared by dissolving methyl 2-hydroxy-2-[2-nitrophenyl]acetate (2.11 g, 10 mmol) in dichloromethane (30 ml). The reaction mixture was cooled to 0° C. and carbonyldiimidazole (1.62 g, 10 mmol) was added. After 2 hr, the reaction mixture was warmed to room temperature, and extracted with water (3×30 ml). The organic layer was dried over MgSo$_{41}$ filtered, and evaporated to give an oil. Crystallization from acetone/isopropyl ether (1:15) gave 1.86 g (61%) of methyl 2-[2-nitrophenyl] acetate-2-oxycarbonylimidazole. A second crop of crystals of equal purity weighed 0.68 g for an overall yield of 83%. mp. 82–85° C. $^1$H-NMR: 8.19 (s, 1H), 8.15 (d, J=8.30 Hz, 1H), 7.78–7.63 (m, 3H), 7.46 (s, 1H), 7.11 (s, 1H), 7.00 (s, 1H), 3.83 (s, 3H). HRMS(EI): calculated for $C_{11}H_{11}N_3O_6$ [M$^+$] m/z=305.0648, observed 305.0663.

1-[2,5-Di(tert-butyl)-4-hydroxyphenyl]-2-[methyl 2-[2-nitrophenyl]acetate-2-yl] carbonate (FIG. 2; Compound 8) (Nmoc-DBHQ/Me) was prepared by adding 2,5-di(tert-butyl)hydroquinone (0.222 g, 1.00 mmol) and 4-dimethylaminopyridine (DMAP) (0.024 g, 0.2 mmol) to a solution of methyl 2-[2-nitrophenyl]acetate-2-oxycarbonylimidazole (0.305 g, 1.00 mmol) in 2.0 ml of DMF. The reaction mixture was maintained at a temperature of 60° C. for 20 hr, cooled, and taken up in ethyl acetate (25 ml). Extraction with water (3×25 ml), followed by drying over MgSO$_4$, and evaporation of solvent gave an oil. Chromatography with hexane/ethyl acetate (4:1), followed by evaporation of solvent gave 0.165 g (36%) of 1-[2,5-di(tert-butyl)-4-hydroxyphenyl]-2-[methyl 2-[2-nitrophenyl] acetate-2-yl] carbonate as a thick oil. $^1$H NMR: 8.12 (d, J=8.19 Hz, 1H), 7.78–7.56 (m, 3H), 6.95 (s, 1H) 6.92 (s, 1H), 6.64 (s, 1H), 4.79 (s, 1H), 3.79 (s, 3H), 1.37 (s, 9H), 1.23 (s, 9H). HRMS(EI): calculated for $C_{24}H_{29}NO_8$ [M$^+$] m/z=459.1893, observed 459.1903.

1-[2,5-Di(tert-butyl)-4-hydroxyphenyl]-2-[2-[2-nitrophenyl]acetic acid-2yl] carbonate (FIG. 2; Compound 2) (Nmoc-DBHQ) was prepared by dissolving 1-[2,5-di(tert-butyl)-4-hydroxyphenyl]-2-[methyl 2-[2-nitrophenyl] acetate-2-yl] carbonate (126 mg, 0.27 mmol) in THF (13 ml) and water (3.0 ml). Sodium hydroxide (1.0 M, 0.55 ml, 0.55 mmol) was added, and the mixture was stirred for 45 min. The solution was acidified with 1.0 M HCl (1.0 ml), and extracted with ethyl acetate (3×3 ml). The organic layer was dried over Na$_2$SO$_4$, filtered, and evaporated to give crude 1-[2,5-di(tert-butyl)-4-hydroxyphenyl]-2-[2-[2-nitrophenyl] acetic acid-2yl] carbonate as an oil. This material could be carried on directly to obtain 1-[2,5-di(tert-butyl)-4-hydroxyphenyl]-2-[acetoxymethyl 2-[2-nitrophenyl] acetate-2-yl] carbonate, or purified by chromatography with hexane/ethyl acetate/acetic acid (40:60:1). $^1$H-NMR: 8.12 (d, J=8.06 Hz, 1H), 7.78–7.57 (m, 3H), 6.93 (s, 1H), 6.63 (s, 1H), 5.30 (s, 1H), 1.35 (s, 9H), 1.29 (s, 9H). HRMS(EI): calculated for $C_{23}H_{27}NO_8$ [M$^+$] m/z=445.1738, observed 445.1764.

1-[2,5-Di(tert-butyl)-4-hydroxyphenyl]-2-[acetoxymethyl 2-[2-nitrophenyl]acetate-2-yl] carbonate (FIG. 2; Compound 9) (Nmoc-DBHQ/AM) was prepared by adding sodium hydroxide (1.0 M, 0.27 ml, 0.27 mmol) to a solution of crude 1-[2,5-di(tert-butyl)-4-hydroxyphenyl]-2-[2-[2-nitrophenyl]acetic acid-2yl] carbonate (entire amount, 0.27 mmol) in ethanol (10 ml). The solvent was removed and the residual water was removed by azeotropic distillation with ethanol (2×10 ml). Dichloromethane (4.0 ml) and tetrabutylammonium iodide (0.10 g, 0.27 mmol) were added to the residue. After stirring for 1 hr, bromomethyl acetate (0.080 ml, 0.82 mmol) was added. The reaction mixture was stirred for an additional hour. The solvent was then evaporated, and the residue was chromatographed with hexane/ethyl acetate (4:1) to give g of 0.085 g (60%) of 1-[2,5-di(tert-butyl)-4-hydroxyphenyl]-2-[acetoxymethyl 2-[2-nitrophenyl]acetate-2-yl] carbonate as an oil. $^1$H-NMR: 8.15 (d, J=7.81 Hz, 1H), 7.76–7.58 (m, 3H), 6.95 (s, 1H), 6.90 (s, 1H), 6.64 (s, 1H), 5.81, (d, J=13.19 Hz, 1H), 5.79 (d, J=13.19 Hz, 1H), 4.82 (bs, 1H), 2.08 (s, 3H), 1.37 (s, 9H), 1.31 (s, 9H). HRMS(EI): calculated for $C_{26}H_{31}NO_{10}$ [M$^+$] m/z=517.1948, observed 517.1966.

EXAMPLE 1

Photoreactivity of Nmoc-DBHO

To demonstrate the photoreactivity of Nmoc-DBHQ, a series of UV-visible absorption spectra were acquired from a solution of the sodium salt of Nmoc-DBHQ that was photolyzed with 365 nm light.

More specifically, using a stirred sample containing 60 $\mu$M of the sodium salt of Nmoc-DBHQ in 150 mM NaCl, 10 mM phosphate buffer (pH 7.2), UV-visible spectra were recorded after the stirred sample had been exposed for 0, 10, 20, 40, 80, 160, 320, 640, and 1290 s to 365 nm light at an intensity of $5.7 \times 10^8$ einst·cm$^{-2}$·s$^{-1}$. UV-visible spectra were recorded on a scanning spectrophotometer (Model Lambda 3B, Perkin-Elmer). Photolysis light intensity was determined by ferrioxalate actinometry (Rabek, In: *Experimental Methods in Photochemistry and Photophysics*, Interscience, Chichester, pages 944–946 (1982)). Output from a 100 W mercury arc lamp (HBO100; Osram, Danvers, Mass.), filtered through 3 mm UG-1 glass to isolate the 365 nm emission, was used for photolysis. The results are shown in FIG. 3A.

Figure 3A:
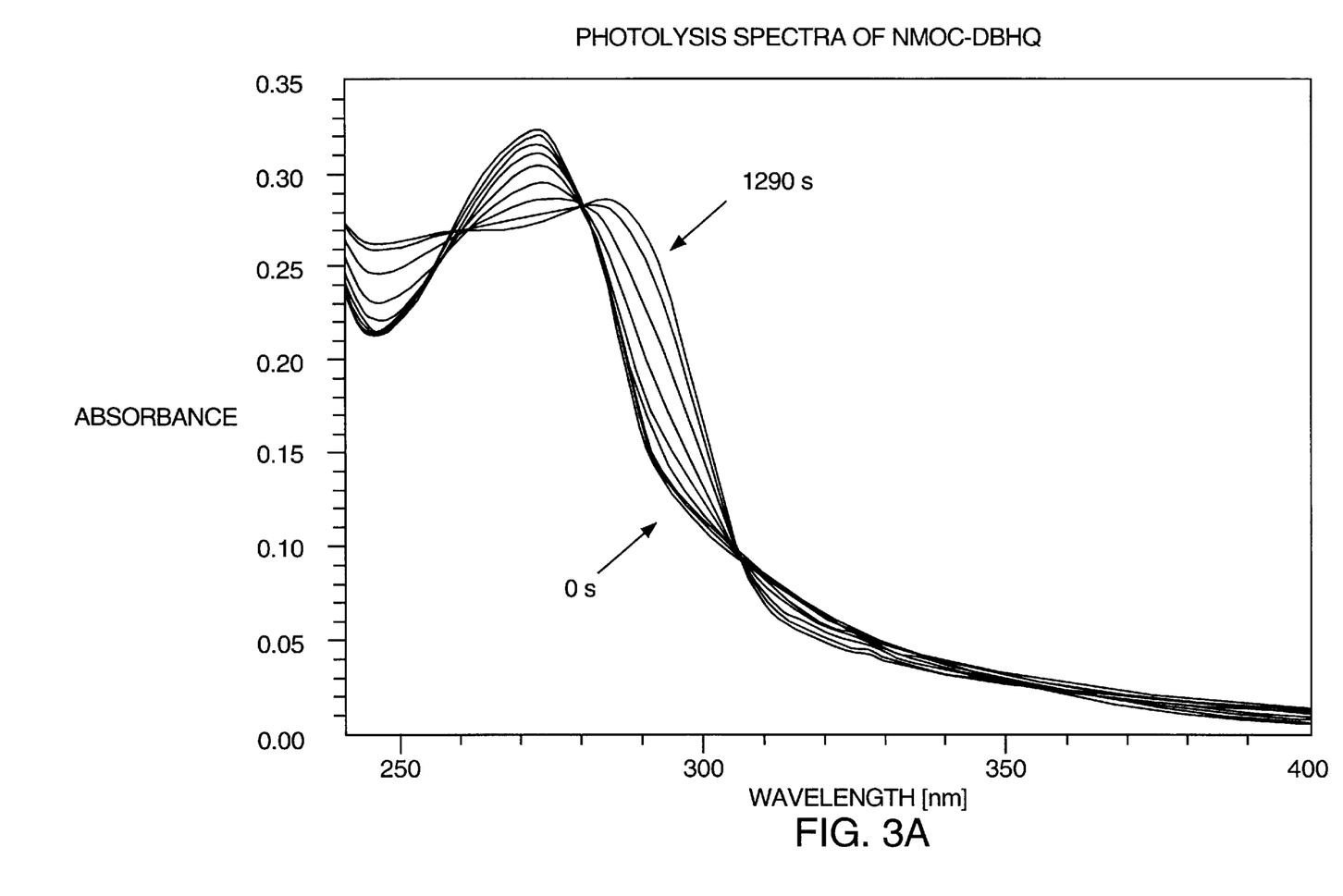
FIGS. 3A and 3B show UV-visible spectra of Nmoc-DBHQ during photolysis (FIG. 3A); and the exponential time course of Nmoc-DBHQ photolysis (FIG. 3B).

As shown in FIG. 3A, the spectroscopic changes resulting from photolysis are consistent with those expected from the classic o-nitrobenzyl rearrangement. In particular, photolysis caused an increase in absorbance at longer wavelengths, a result of the long-wavelength absorption by the highly conjugated byproduct (FIG. 1).

Because the spectra show good isosbestic points through the course of photolysis, the quantum efficiency of photolysis of Nmoc-DBHQ was next determined by analyzing the absorbance changes as a function of time. Determination of quantum yield (Q) of photolysis from UV-visible spectra collected after intervals of photolysis with a calibrated UV source was performed as described by Adams et al, supra; and Livingston et al, In: *Techniques of Chemistry.*, Vol. 3: Photochromism, Brown, G. H., Ed., Wiley, New York, pages 13–44 (1971). The results are shown in FIG. 3B.

Figure 3B:
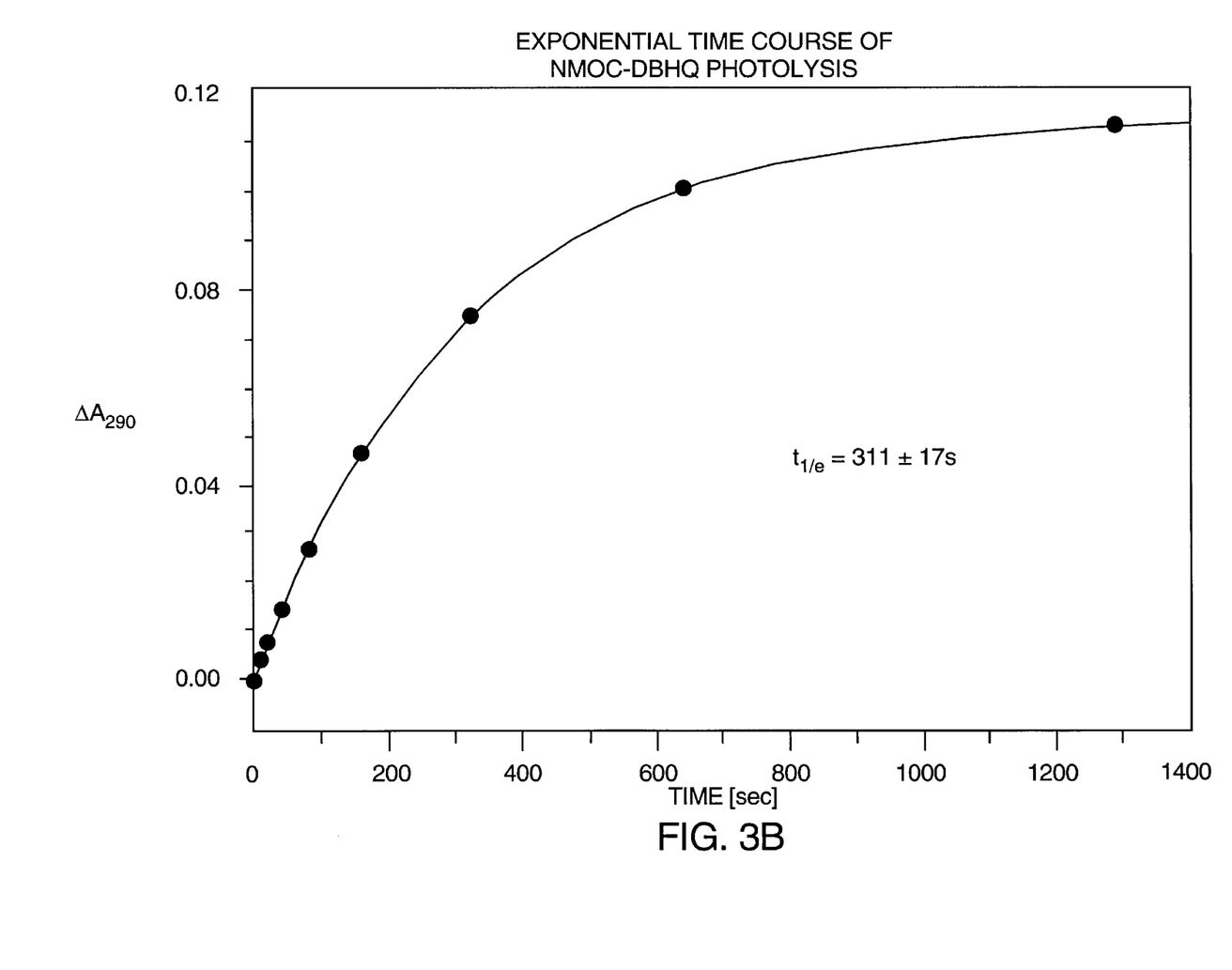

FIG. 3B shows a graph of $\Delta A_{290}$, the change in absorbance of the sample at 290 nm (taken from the spectra shown in FIG. 3A), as a function of time of photolysis by light of known intensity, $I_0$. The data are well fit by a single exponential with characteristic time constant ($\tau$) of 311±17 s. The quantum yield of photolysis of Nmoc-DBHQ was thus determined to be $Q=2.303 I_0 \epsilon_{365} \tau = 0.10$ (Adams et al, supra; and Livingston, supra).

Next, the kinetics for photolytic removal of the caging group were examined by monitoring the transient absorbance changes characteristic of the short-lived aci-nitro intermediate generated during photolysis of o-nitrobenzyl moieties (Schupp et al, *J. Photochem.*, 36:85–97 (1987); Yip et al, *J. Phys. Chem.*, 89:5328–5330 (1985); Yip et al, *J. Phys. Chem.*, 95:6078–6081 (1991); and Zhu et al, *J. Photochem.*, 39:317–332 (1987)).

More specifically, a 660 $\mu$M solution of the sodium salt of Nmoc-DBHQ was prepared in 150 mM NaCl, 10 mM phosphate (pH 7.2). The stirred solution was photolyzed with 308 nm, 100 mJ, 10 ns pulsed emission from a XeCl excimer laser (Questek 2110) while the absorbance of the solution at 440 nm was measured. By monitoring the appearance and decay of the absorbance due to the aci-nitro intermediate generated by photolysis, the kinetics of uncaging could be examined (McCray et al, *Ann. Rev. Biophys. Biophys. Chem.*, 18:239–270 (1989); and Walker et al, *J. Am. Chem. Soc.*, 110:7170–7177 (1988)). In some runs, the experimental solution was continuously purged with nitrogen gas, although purging produced no observable difference in the kinetic behavior of the system. The results are shown in FIG. 4, which is a trace of the sum of 45 individual pulse experiments.

Figure 4:
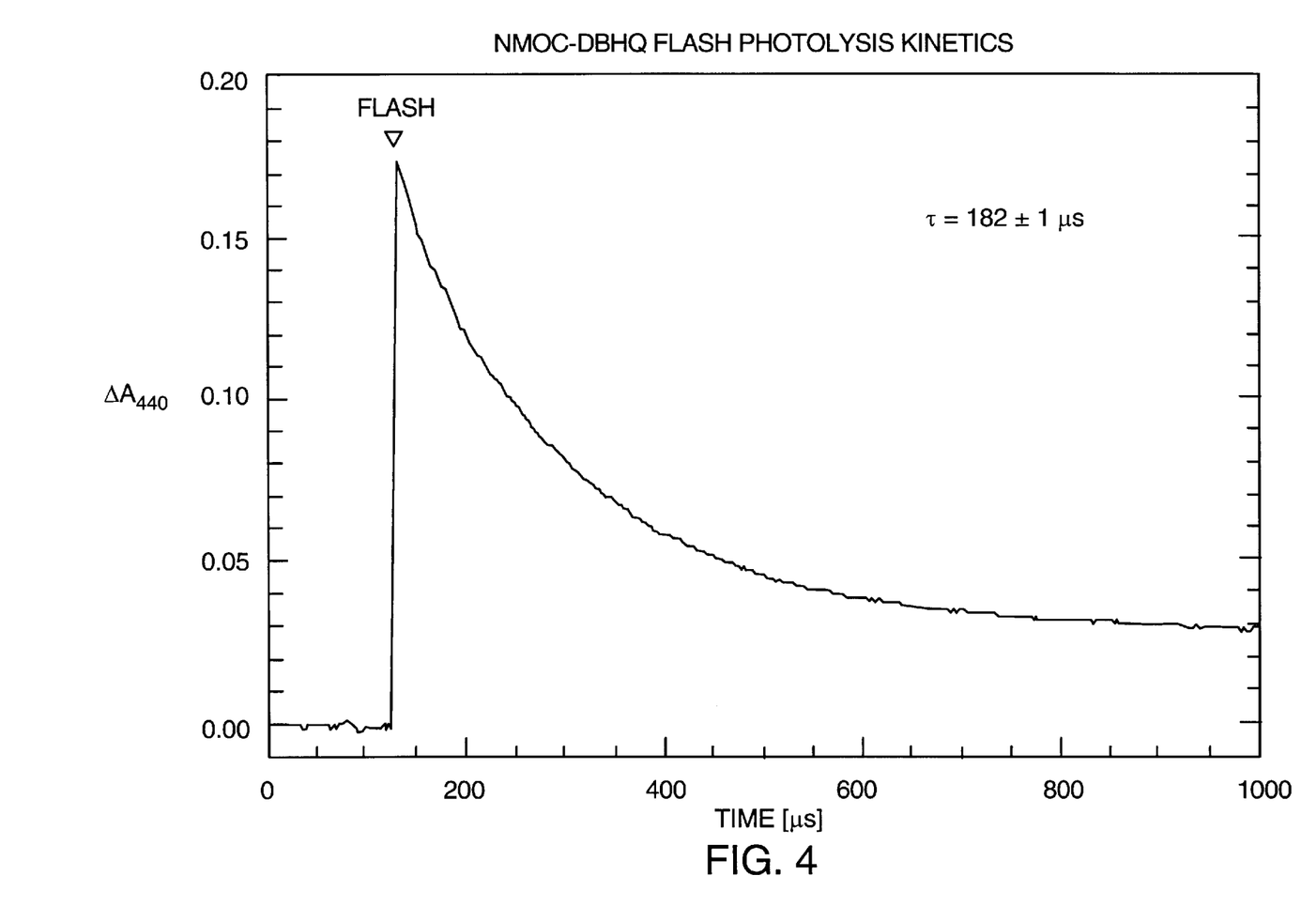
FIG. 4 shows the transient absorbance changes following pulsed laser photolysis of Nmoc-DBHQ.

As shown in FIG. 4, the decay comprises two exponential components. The faster component has a time constant of 29±2 $\mu$s. The slower, dominant component, which accounts for >91% of the total amplitude, is characterized by a time constant, i.e., lifetime ($\tau$) of 182±1 $\mu$s. There is a small contribution at short times from a fast minor component. These results imply that the photochemical cleavage reaction is essentially complete in approximately 550 $\mu$s, i.e., in about three lifetimes. The trace in FIG. 4 does not return to the pre-photolysis baseline because the byproduct nitrosoketone absorbs more strongly than the starting material at wavelength longer than ~360 nm (compare pre- and post-photolysis spectra in FIG. 3A)

Photocleavage of the nitromandelyl moiety leaves the carbonate mono-ester of DBHQ (FIG. 1), which must lose $CO_2$ to liberate DBHQ. Although the rate of decarboxylation, $k_{dec}$, cannot be measured in the present system, it can be estimated from published studies of similar reactions. The decarboxylation rate ($k_{dec}$) of carbonate mono-esters has been shown to follow the relationship: $\log(k_{dec})=15.1-1.16 pK_a$, where $pK_a$ is the $pK_a$ of the hydroxyl group that is esterified to the carbonate (Sauers et al, *J. Am. Chem. Soc.*, 97:5546–5553 (1975); and Pocker et al, *J. Am. Chem. Soc.*, 100:3564–3567 (1978)). Since the $pK_a$ of DBHQ is estimated to be 11.21 (Perrin et al, $pK_a$ Prediction for *Organic Acids and Bases*, Chapman and Hall, London (1981)), the rate constant for decomposition of the carbonate mono-ester of DBHQ is expected to be $k_{dec} \approx 130$ s$^{-1}$ ($t_{1/2} \approx 5.3$ ms) at 25° C.

EXAMPLE 2

In vivo Photorelease of DBHQ

The biological efficacy of Nmoc-DBHQ was tested in living cells loaded simultaneously with Nmoc-DBHQ and the fluorescent Ca$^{2+}$ indicator, Fluo-3. Fluo-3 allows one to determine the effects of photoreleasing DBHQ on intracellular Ca$^{2+}$ dynamics, which can be monitored through the Ca$^{2+}$-sensitive fluorescence of Fluo-3.

More specifically, Fisher rat embryo fibroblasts of the cell line REF52 were cultured on 25 mm diameter glass coverslips as described by Kao et al, *J. Biol. Chem.*, 264:8179–8184 (1989). In addition, acutely dissociated neurons from the nodose ganglia of ferret were prepared and plated onto 25 mm diameter glass coverslips coated with poly-D-lysine as described by Jafri et al, *J. Physiol.*, 493:157–166 (1986).

Cells were coloaded with indicator and caged reagent by incubation for 60–80 min at room temperature with medium containing 2.0–5.0 $\mu$M Fluo-3/AM (Molecular Probes; Eugene, Oreg.), 20–40 $\mu$M Nmoc-DBHQ/AM, and less than 0.015% (w/v) of the surfactant Pluronic F-127 (Molecular Probes; Eugene, OR) to enhance the aqueous solubility of the AM esters. Fluo-3/AM, Nmoc-DBHQ/AM, and Pluronic F-127 were kept frozen as, respectively, 5.0 mM, 40 mM, and 15% (w/v) stock solutions in dry dimethylsulfoxide (DMSO) until use. For loading, Dulbecco's Modified Eagle's Medium (DME) buffered with HEPES (pH 7.4) was used for the REF52 cells, and Leibovitz L-15 medium containing 10% (v/v) fetal bovine serum and buffered at pH 7.4 was used for the nodose neurons. After loading, coverslips bearing the cells were washed with fresh medium, and mounted in culture dishes charged with 4.0 ml experimental medium. The experiments with the REF52 cells were conducted in Hanks' Balanced Salt Solution (HBSS) at room temperature, while HEPES-buffered Locke solution was used for the nodose neurons.

Cells were positioned on the stage of an inverted microscope (Diaphot, Nikon) equipped with a dichroic mirror that transmits at wavelengths longer than 500 nm but has high reflectance in the UV and 450–500 nm range so that photolysis and epifluorescence measurements could be performed simultaneously. A spectrofluorometer (CM1T10I; SPEX Industries), fitted with a 450 W xenon arc lamp, was coupled to the microscope epifluorescence port through a fiberoptic cable and was operated in the microfluorometry mode. Fluo-3 was excited by 500 nm light (4 nm bandwidth) from a monochromator, while its emission, collected through the microscope objective (UV-F, ×40, N.A. 1.3, Nikon), after passing through a 530 nm bandpass filter, was sampled by a photomultiplier tube, the output from which was digitized and stored for subsequent analysis. Instrument control, data acquisition and analysis were performed through DM3000CM software (SPEX Industries) running on a dedicated personal computer.

Output from a 50 W mercury arc lamp (HBO50; Osram), filtered through 2.0 mm UG-1 glass to isolate UV light in the 300–400 nm range, was used for flash photolysis conducted in parallel with microfluorometry. A 400 nm long-pass dichroic mirror was placed so that it was colinearly aligned with the epifluorescence port and the dichroic mirror underneath the microscope objective and served to guide the photolysis beam into the optical path of the microscope. The photolytic light traversed a path of approximately 38 cm, as measured from the mercury arc to the sample above the objective. An electromechanical shutter (Vincent Associates, Rochester, N.Y.) was used to control UV light exposure. During photolysis, fluorescence data collection was interrupted by a second shutter to prevent damage to the photomultiplier. The results are shown in FIGS. 5A (DBHQ photorelease experiments performed in rat embryo fibroblasts); and in FIG. 5B (DBHQ photorelease experiments performed in acutely isolated nodose neurons of adult ferret).

Figure 5A:
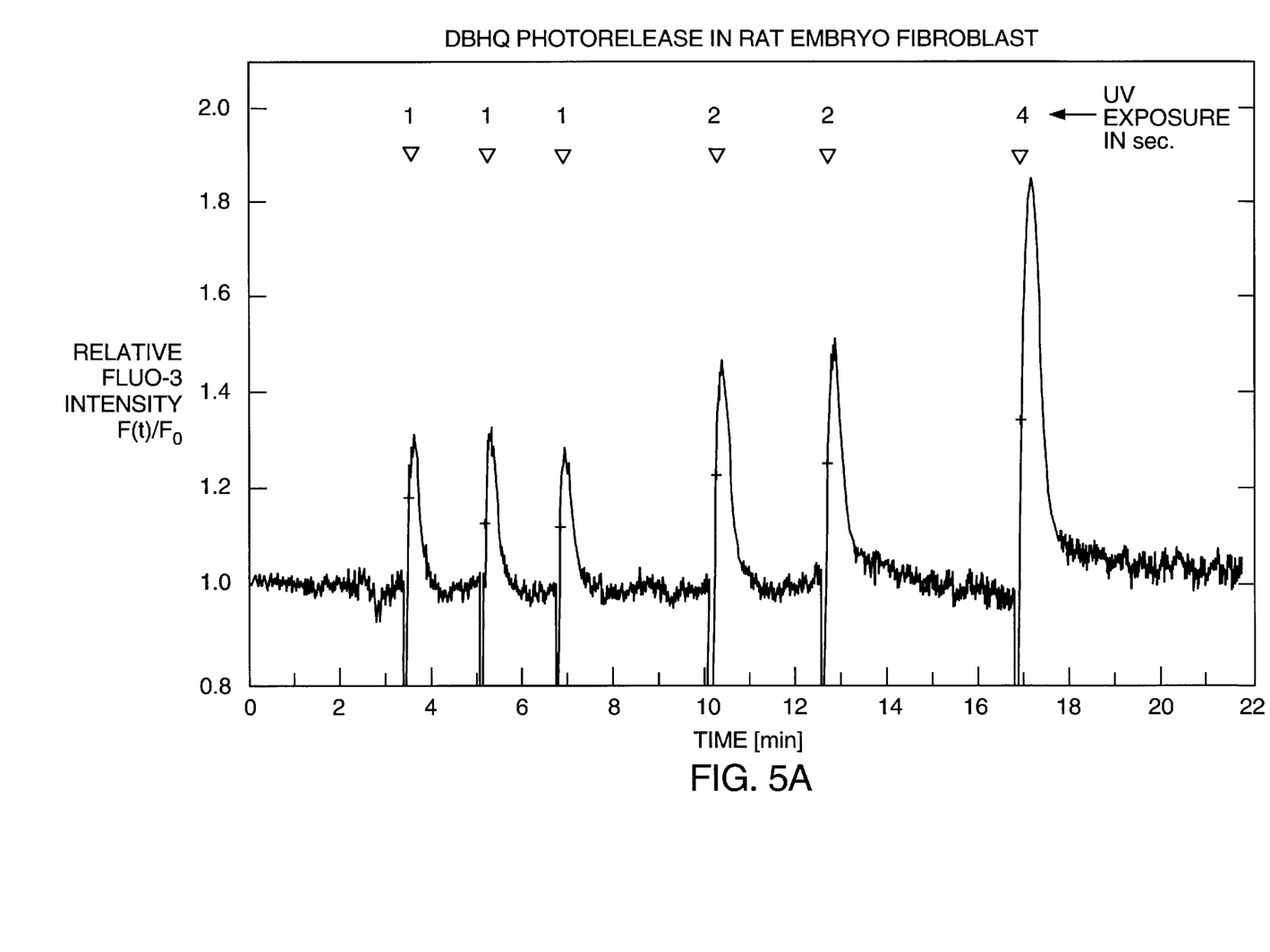
FIGS. 5A and 5B show the effects of DBHQ photorelease on $[Ca^{2+}]_i$ in rat embryo fibroblasts (FIG. 5A), and ferret nodose neurons (FIG. 5B).
Figure 5B:
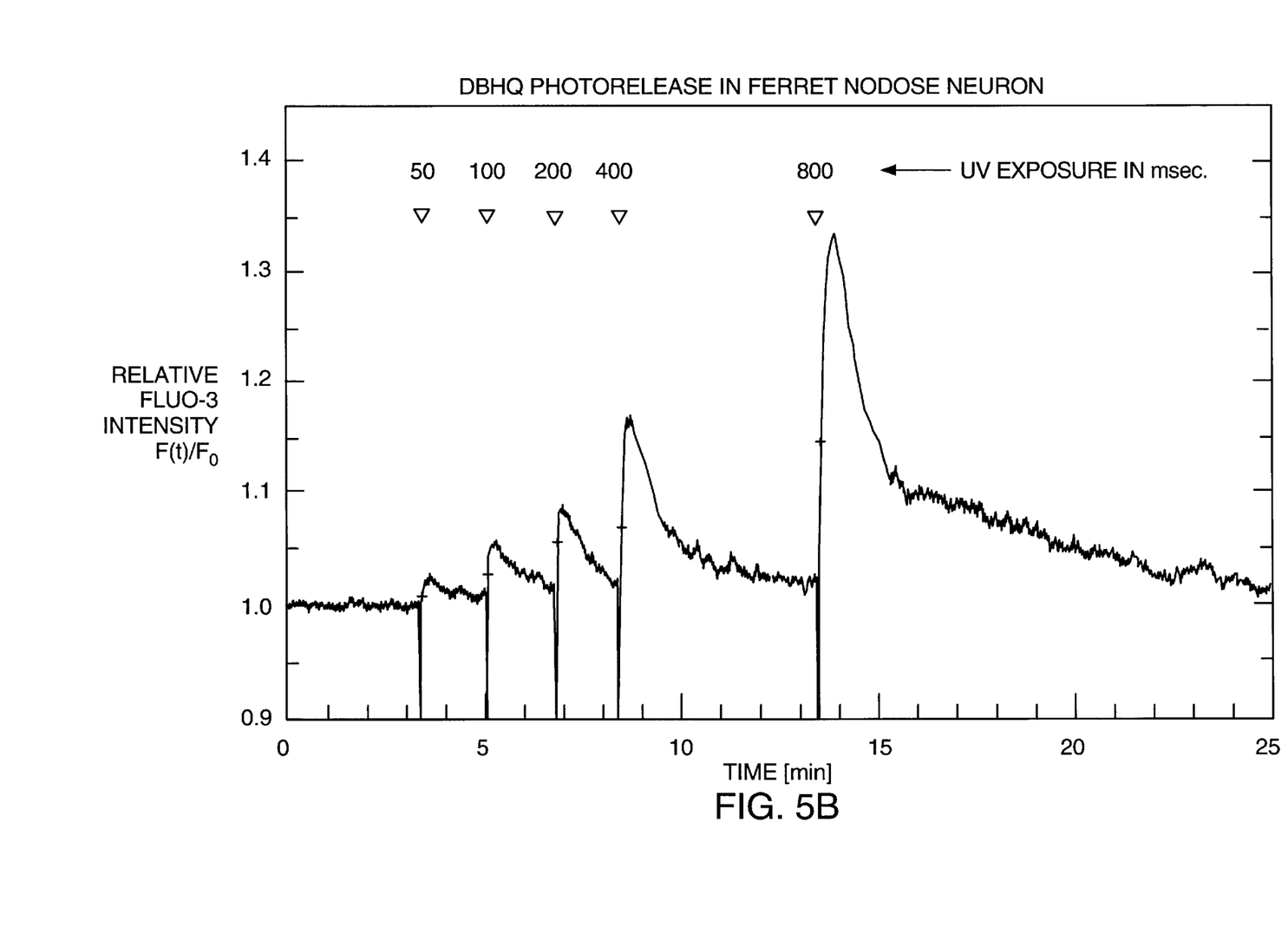

The data in FIGS. 5A and 5B show that photorelease of DBHQ within cells lead to rapid, dose-dependent transient increases in $[Ca^{2+}]_i$. The resting cytosolic $[Ca^{2+}]$ is maintained through a dynamic balance of active pumping processes that remove $Ca^{2+}$ from the cytosol, and passive leaks that introduce $Ca^{2+}$ into the cytosol. When photoreleased DBHQ disrupts the pump-leak balance by inhibiting the SERCA pumps, an increase in $[Ca^{2+}]_i$ is observed. The $[Ca^{2+}]_i$ rise is transient because SERCA inhibition by DBHQ is reversible and because free DBHQ is a small, uncharged, membrane-permanent molecule that is cleared from the cell by diffusion. Once DBHQ diffuses out of the cell and is lost to the bathing medium, inhibition of the SERCA pumps ceases and the resting $[Ca^{2+}]_i$ is reestablished.

A comparison of the results from rat fibroblasts and ferret nodose neurons (FIGS. 5A and 5B, respectively) shows that the kinetics of onset of the response to DBHQ photorelease are similar for the two cell types (rise times of 7.8±3.4 s and 6.2±2.4 s, respectively). In contrast, decay of the response to photorelease appears more protracted in the nodose neuron. Whereas $t_{1/2}$ for recovery from photorelease is of the order of 10–15 s in the fibroblast, in the nodose neuron the value increases to 40–50 s. The different kinetics of recovery likely reflect differences in the surface-to-volume ratios of the two cell types. Whereas the fibroblasts are an adherent cell in monolayer culture with flat, extended morphology, and are at most a few microns in thickness, the acutely dissociated nodose neurons are spherical, with a diameter of ~55 $\mu$m (Jafri et al supra). Clearance of photoreleased DBHQ from the cell interior by diffusion is thus expected to be slower for the nodose neurons than for the fibroblasts.

To demonstrate the usefulness of Nmoc-DBHQ in manipulating dynamic cellular phenomena, Nmoc-DBHQ was used to perturb $[Ca^{2+}]_i$ oscillations. The oscillations were initiated by bath application to the rat fibroblasts of 500 nM $R^8$-vasopressin (Sigma; St. Louis, Mo.), followed by 500 nM gramicidin D (Sigma; St. Louis, Mo.). The results are shown in FIGS. 6A and 6B.

Figure 6A:
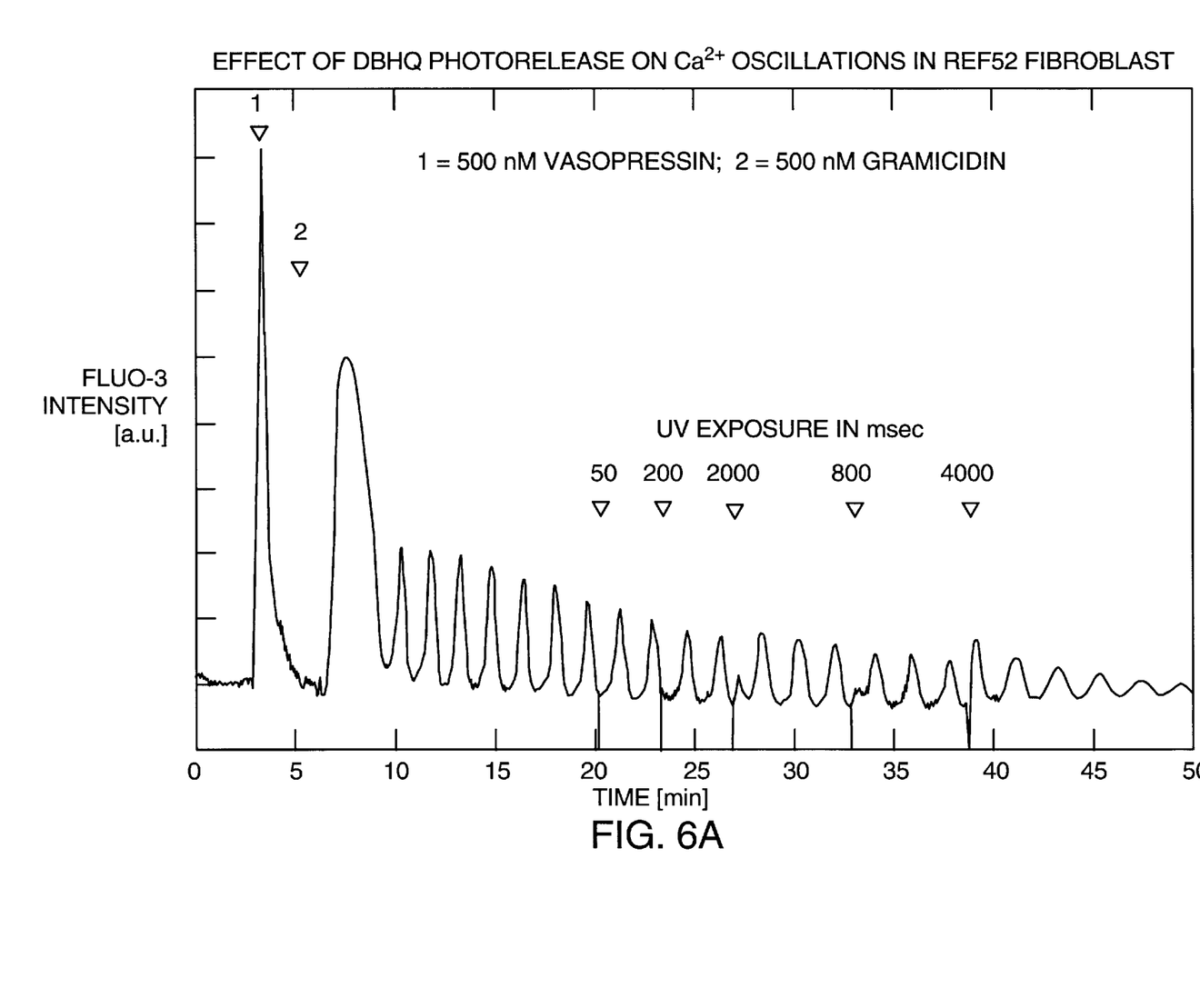
FIGS. 6A and 6B show the use of DBHQ photorelease to perturb intracellular $[Ca^{2+}]$ oscillations in REF52 rat embryo fibroblasts. The full fluorescence trace of an experiment in which oscillations in $[Ca^{2+}]_i$ were elicited in REF52 fibroblasts, and then perturbed by pulses of DBHQ photorelease, is shown in FIG. 6A; and an expanded plot of a portion of the trace in FIG. 6A is shown in FIG. 6B to more clearly demonstrate the effect of DBHQ photorelease on the timing of the oscillations.
Figure 6B:
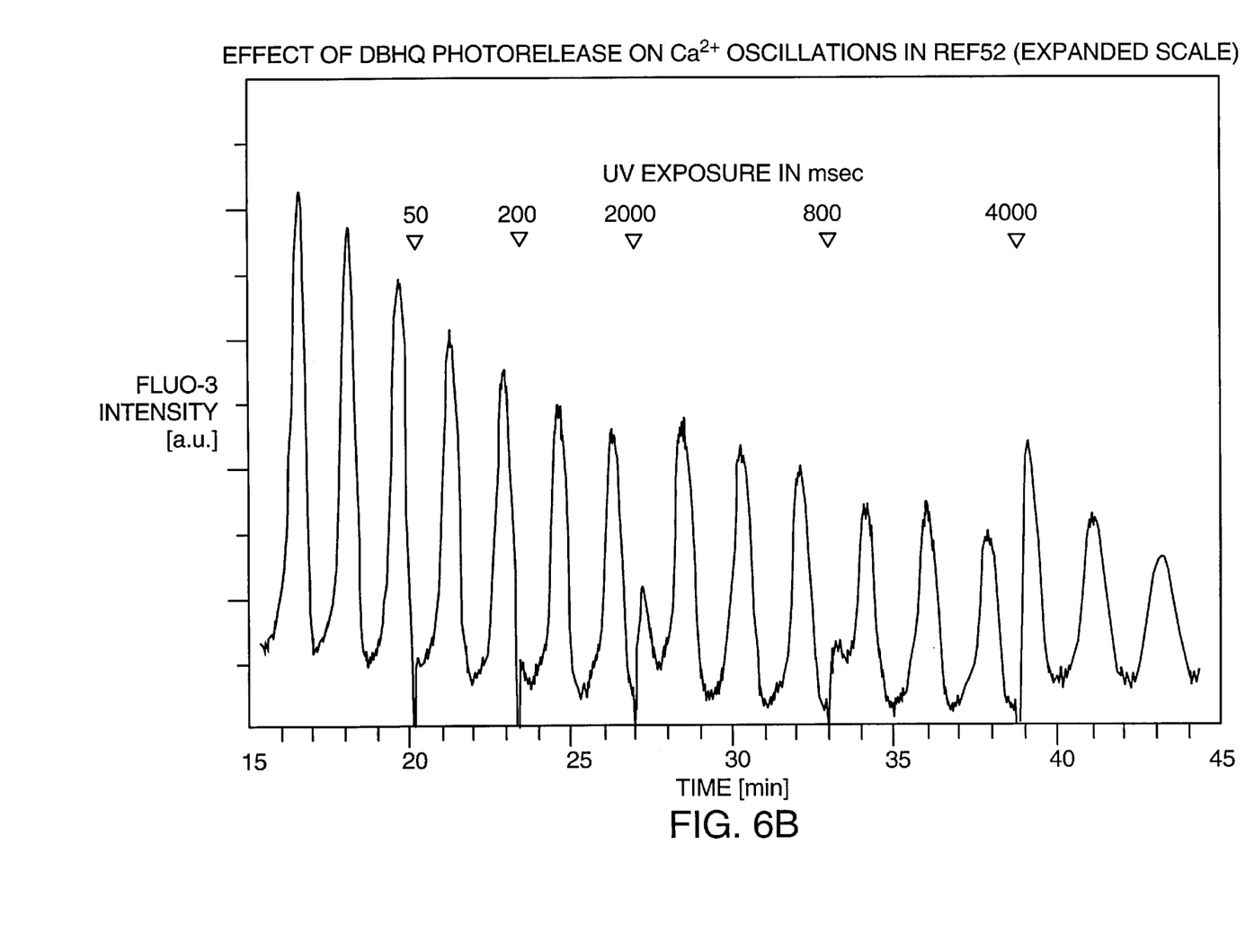

As shown in FIG. 6A, highly regular calcium oscillations were initiated in REF52 fibroblasts by activation of the inositol trisphosphate signaling pathway coupled with depolarization (Harootunian et al, *Cold Spring Harbor Symp. Quant. Biol.*, 53:935–943 (1988)). In addition, it can be seen from FIG. 6B that pulsed inhibition of the SERCA pump produces distinct changes in the timing of $[Ca^{2+}]$ oscillations. The perturbation effects are the result of photorelease, and are not observed when light flashes are delivered in the absence of caged reagent, as has been demonstrated previously (Harootunian et al, (1991a) supra; Harootunian et al, (1991b) supra; and Harootunian et al, (1988) supra). Specifically, transient SERCA inhibition by DBHQ photorelease causes a delay in the occurrence of the next endogenous oscillation peak. Alternatively stated: DBHQ photorelease during an oscillation cycle increases the period of that cycle. The extent of period lengthening is in proportion to the amount of photorelease-with short light flashes producing only slight delays, while long flashes can cause significant period lengthening (FIG. 6B). Such quantitative information is believed to be useful for constructing, as well as validating, biophysical models of intracellular $Ca^{2+}$ dynamics (see e.g., Harootunian et al, (1991a) supra; and Harootunian et al, (1991b) supra).

Conventional means for rapidly delivering drugs or reagents to living cells typically involves superfusing a solution containing the desired drug or reagent over the cells. The speed of delivery is limited by two factors: (1) the rate at which an aqueous solution can flow through the experimental chamber containing the living cells, and (2) the rate at which the drug or reagent molecules are able to penetrate into the interior of cells. Such rate limitations imply that reagent application by superfusion usually gives rise to a delay between reagent application and the elicited response from a living cell. Directly generating a reagent or drug in situ by photolysis of caged molecules trapped within cells eliminates the rate limitations inherent to superfusion and, therefore, should elicit much faster responses. To demonstrate such, a comparison of the kinetics of changes in intracellular free $[Ca^{2+}]$ elicited in a REF52 fibroblasts by DBHQ delivered via either superfusion or photolysis was carried out. More specifically, cytosolic $[Ca^{2+}]$ was monitored with the indicators fluo-3 and fura-2, for DBHQ photorelease and DBHQ superfusion, respectively. For DBHQ photorelease, the cell was loaded with Nmoc-DBHQ and fluo-3 indicator by incubation with 40 $\mu$M Nmoc-DBHQ/AM and 5.0 $\mu$M fluo-3/AM for 1 hr. For DBHQ superfusion, the cell was loaded with fura-2 indicator by incubation with 1.0 µM of the AM ester for 1 hr; the DBHQ superfusate solution was used at a concentration of 60 µM. DBHQ photorelease was affected by a 1 s UV flash from a 100 W mercury arc lamp, the output of which was filtered through 3.0 mm UG1 glass. Superfusion was affected by a 1 s delivery of DBHQ solution. The results are shown in FIG. 7.

Figure 7:
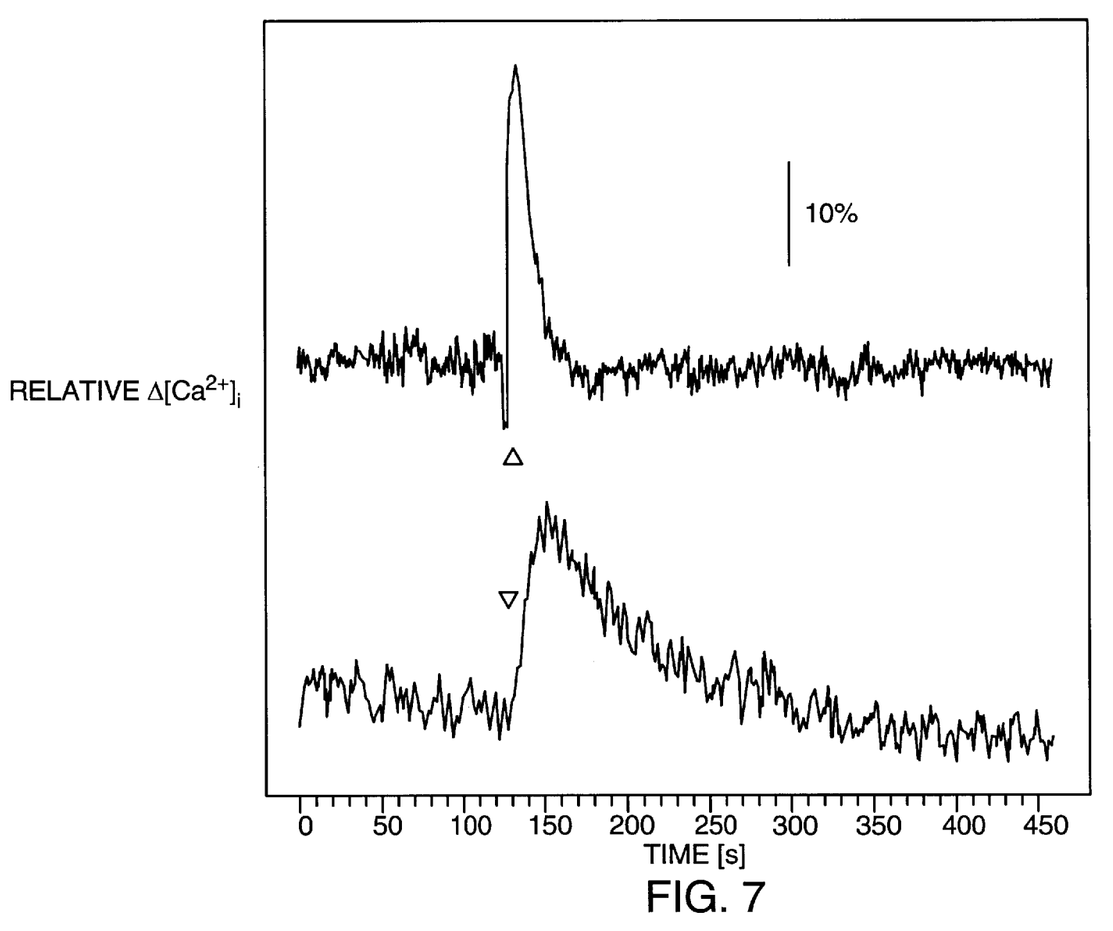
FIG. 7 shows a comparison of the kinetics of changes of intracellular (cytosolic) free $[Ca^{2+}]$ in REF52 rat embryos fibroblasts in response to DBHQ application by photorelease (upper tract) and by superfusion (lower tract). The scale bar represents a 10% change in cytosolic $[Ca^{2+}]$. Arrow heads mark the beginnings of the 1 s DBHQ applications.

As shown in FIG. 7, photoreleasing DBHQ directly in the cell elicited a response that peaked and subsided much more rapidly than the response resulting from superfusion of DBHQ.

As demonstrated above, in the present invention, Nmoc-DBHQ, a caged inhibitor of the SERCA pump, has been synthesized and characterized. Photolysis of Nmoc-DBHQ proceeds with $t_{1/2}=126\pm2$ µs, and $t_{1/2}$ for subsequent release of DBHQ is estimated to be ~5 ms. Thus, Nmoc-DBHQ allows rapid and reversible modulation of the SERCA activity in living cells, and is useful for probing systems whose rapidly varying $Ca^{2+}$ dynamics make study inaccessible through conventional techniques of reagent delivery. Further, through its acetoxymethyl (AM) ester, Nmoc-DBHQ can be loaded into cells easily by incubation.

While the invention has been described in detail, and with reference to specific embodiments thereof, it will be apparent to one of ordinary skill in the art that various changes and modifications can be made therein without departing from the spirit and scope thereof.

What is claimed:

1. A compound represented by structural Formula:

wherein Z is selected from the group consisting of $CO_2R^1$, $SO_3R^1$ and $PO_3R^1{}_2$;

wherein $R^1$ is selected from the group consisting of hydrogen, an alkyl group having from 1 to 5 carbon atoms, an alkali metal, $NH_4$, and $CH_2O_2CCH_3$; and wherein $R^2$, $R^3$ and $R^4$, which may be the same or different, are each selected from the group consisting of hydrogen, an alkyl group having from 1 to 5 carbon atoms, F, Cl, Br, CN, $NO_2$, $CO_2R^5$, $OR^5$, and $OCH_2CO_2R^5$, wherein $R^5$ is selected from the group consisting of hydrogen, an alkyl group having from 1 to 5 carbon atoms, an alkali metal, $NH_4$, and $CH_2O_2CCH_3$; and wherein optionally, $R^3$ and $R^4$ together form a $(O\!-\!(CH_2)_n\!-\!O)$ linkage, wherein n represents an integer of from 1 to 4.

2. The compound of claim 1, wherein Z is $CO_2R^1$, $R^1$ is selected from the group consisting of hydrogen, Na, K, methyl, ethyl, and $CH_2O_2CCH_3$, $R^2$ is hydrogen or $NO_2$, $R^3$ and $R^4$ are each selected from the group consisting of hydrogen and methoxy, or when $R^3$ and $R^4$ are combined, methylenedioxy ($-OCH_2O-$).

3. The compound of claim 1, wherein said compound is selected from the group consisting of 1-[2,5-Di(tert-butyl)-4-hydroxyphenyl]-2-[2-[2-nitrophenyl]acetic acid-2-yl] carbonate (Nmoc-DBHQ), 1-[2,5-Di(tert-butyl)-4-hydroxyphenyl]-2-[methyl 2-[2-nitrophenyl]acetate-2-yl] carbonate (Nmoc-DBHQ/Me), 1-[2,5-Di(tert-butyl)-4-hydroxyphenyl]-2-[ethyl 2-[2-nitrophenyl]acetate-2-yl] carbonate (Nmoc-DBHQ/Et), 1-[2,5-Di(tert-butyl)-4-hydroxyphenyl]-2-[sodium 2-[2-nitrophenyl]acetate-2-yl] carbonate (Nmoc-DBHQ/Na), 1-[2,5-Di(tert-butyl)-4-hydroxyphenyl]-2-[potassium 2-[2-nitrophenyl]acetate-2-yl] carbonate (Nmoc-DBHQ/K), 1-[2,5-Di(tert-butyl)-4-hydroxyphenyl]-2-[acetoxymethyl 2-[2-nitrophenyl]acetate-2-yl] carbonate (Nmoc-DBHQ/AM), 1-[2,5-Di(tert-butyl)-4-hydroxyphenyl]-2-[2-[4,5-methylenedioxy-2-nitrophenyl]acetic acid-2-yl] carbonate, 1-[2,5-Di(tert-butyl)-4-hydroxyphenyl]-2-[methyl 2-[4,5-methylenedioxy-2-nitrophenyl]acetate-2-yl] carbonate, 1-[2,5-Di(tert-butyl)-4-hydroxyphenyl]-2-[ethyl 2-[4,5-methylenedioxy-2-nitrophenyl]acetate-2-yl] carbonate, 1-[2,5-Di(tert-butyl)-4-hydroxyphenyl]-2-[sodium 2-[4,5-methylenedioxy-2-nitrophenyl]acetate-2-yl] carbonate, 1-[2,5-Di(tert-butyl)-4-hydroxyphenyl]-2-[potassium 2-[4,5-methylenedioxy-2-nitrophenyl]acetate-2-yl] carbonate, and 1-[2,5-Di(tert-butyl)-4-hydroxyphenyl]-2-[acetoxymethyl 2-[4,5-methylenedioxy-2-nitrophenyl]acetate-2-yl] carbonate.

4. A composition comprising the compound of claim 1, wherein said compound is present in an aqueous solution at a concentration of about $10^{-5}$ to $10^{-1}$ M.

5. The composition of claim 4, wherein said aqueous solution has a pH of about 6 to 8.

6. A method for producing 2,5,-di(tert-butyl) hydroquinone (DBHQ) comprising the step of UV irradiating a compound represented by structural Formula (I):

wherein Z is selected from the group consisting of $CO_2R^1$, $SO_3R^1$ and $PO_3R^1{}_2$;

wherein $R^1$ is selected from the group consisting of hydrogen, an alkyl group having from 1 to 5 carbon atoms, an alkali metal, $NH_4$, and $CH_2O_2CCH_3$; and wherein $R^2$, $R^3$ and $R^4$, which may be the same or different, are each selected from the group consisting of hydrogen, an alkyl group having from 1 to 5 carbon atoms, F, Cl, Br, CN, $NO_2$, $CO_2R^5$, $OR^5$, and $OCH_2CO_2R^5$, wherein $R^5$ is selected from the group consisting of hydrogen, an alkyl group having from 1 to 5 carbon atoms, an alkali metal, $NH_4$, and $CH_2O_2CCH_3$; and wherein optionally, $R^3$ and $R^4$ together form a $(O\!-\!(CH_2)_n\!-\!O)$ linkage, wherein n represents an integer of from 1 to 4, and recovering DBHQ.

7. The method of claim 6, wherein Z is $CO_2R^1$, $R^1$ is selected from the group consisting of hydrogen, Na, K, methyl, ethyl, and $CH_2O_2CCH_3$, $R^2$ is hydrogen or $NO_2$, $R^3$ and $R^4$ are each selected from the group consisting of hydrogen and methoxy, or when $R^3$ and $R^4$ are combined, methylenedioxy ($-OCH_2-$).

8. The method of claim 6, wherein said compound is selected from the group consisting of 1-[2,5-Di(tert-butyl)-4-hydroxyphenyl]-2-[2-[2 -nitrophenyl]acetic acid-2-yl] carbonate (Nmoc-DBHQ), 1-[2,5-Di(tert-butyl)-4-hydroxyphenyl]-2-[methyl 2-[2-nitrophenyl]acetate-2-yl]

carbonate (Nmoc-DBHQ/Me), 1-[2,5-Di(tert-butyl)-4-hydroxyphenyl]-2-[ethyl 2-[2-nitrophenyl]acetate-2-yl] carbonate (Nmoc-DBHQ/Et), 1-[2,5-Di(tert-butyl)-4-hydroxyphenyl]-2-[sodium 2-[2-nitrophenyl]acetate-2-yl] carbonate (Nmoc-DBHQ/Na), 1-[2,5-Di(tert-butyl)-4-hydroxyphenyl]-2-[potassium 2-[2-nitrophenyl]acetate-2-yl] carbonate (Nmoc-DBHQ/K), 1-[2,5-Di(tert-butyl)-4-hydroxyphenyl]-2-[acetoxymethyl 2-[2-nitrophenyl]acetate-2-yl] carbonate (Nmoc-DBHQ/AM), 1-[2,5-Di(tert-butyl)-4-hydroxyphenyl]-2-[2-[4,5-methylenedioxy-2-nitrophenyl]acetic acid-2-yl] carbonate, 1-[2,5-Di(tert-butyl)-4-hydroxyphenyl]-2-[methyl 2-[4,5-methylenedioxy-2-nitrophenyl]acetate-2-yl] carbonate, 1-[2,5-Di(tert-butyl)-4-hydroxyphenyl]-2-[ethyl 2-[4,5-methylenedioxy-2-nitrophenyl]acetate-2-yl] carbonate, 1-[2,5-Di(tert-butyl)-4-hydroxyphenyl]-2-[sodium 2-[4,5-methylenedioxy-2-nitrophenyl]acetate-2-yl] carbonate, 1-[2,5-Di(tert-butyl)-4-hydroxyphenyl]-2-[potassium 2-[4,5-methylenedioxy-2-nitrophenyl]acetate-2-yl] carbonate, and 1-[2,5-Di(tert-butyl)-4-hydroxyphenyl]-2-[acetoxymethyl 2-[4,5-methylenedioxy-2-nitrophenyl]acetate-2-yl] carbonate.

9. The method of claim 6, wherein said irradiating is carried out at a wavelength of about 300 to 400 nm.

10. The method of claim 6, wherein said irradiating is carried out at about 10 to 40° C.

11. The method of claim 6, wherein said compound is present in an aqueous solution at a concentration of about $10^{-5}$ to $10^{-1}$ M.

12. The method of claim 11, wherein said aqueous solution has a pH of about 6 to 8.

13. The method of claim 6, wherein tissue or cells are perfused with an aqueous solution comprising said compound and said tissue or cells containing said compound are subjected to said UV irradiation.

14. The method of claim 6, wherein a cell is microinjected with an aqueous solution comprising said compound and said cell containing said compound is subjected to said UV irradiation.

* * * * *

UNITED STATES PATENT AND TRADEMARK OFFICE
CERTIFICATE OF CORRECTION

PATENT NO. : 6,043,065

DATED : March 28, 2000

INVENTOR(S) : Joseph P.Y. KAO, Francis M. ROSSI, Paul F. KEITZ

It is certified that error appears in the above-identified patent and that said Letters Patent is hereby corrected as shown below:

Column 8, line 2, change "$MgSO_{41}$" to -- $MgSO_4$, --.

Column 9, line 8, change "DBHO" to --DBHQ--.

Signed and Sealed this

Tenth Day of April, 2001

Attest:

NICHOLAS P. GODICI

Attesting Officer     Acting Director of the United States Patent and Trademark Office